United States Patent
Takeuchi et al.

(10) Patent No.: US 9,796,751 B2
(45) Date of Patent: Oct. 24, 2017

(54) GLYCYRRHETINIC ACID DERIVATIVE AND USE THEREOF

(71) Applicants: Hideyuki Takeuchi, Kanagawa (JP); INI CORPORATION, Aichi (JP); Akio Suzumura, Aichi (JP)

(72) Inventors: Hideyuki Takeuchi, Kanagawa (JP); Akio Suzumura, Aichi (JP)

(73) Assignees: INI CORPORATION (JP); Hideyuki Takeuchi (JP); Akio Suzumura (JP)

( * ) Notice: Subject to any disclaimer, the term of this patent is extended or adjusted under 35 U.S.C. 154(b) by 0 days.

(21) Appl. No.: 15/038,970

(22) PCT Filed: Nov. 20, 2014

(86) PCT No.: PCT/JP2014/080732
§ 371 (c)(1),
(2) Date: May 24, 2016

(87) PCT Pub. No.: WO2015/076325
PCT Pub. Date: May 28, 2015

(65) Prior Publication Data
US 2016/0376303 A1  Dec. 29, 2016

(30) Foreign Application Priority Data
Nov. 25, 2013  (JP) .................. 2013-243130

(51) Int. Cl.
C07J 63/00  (2006.01)
C07J 53/00  (2006.01)

(52) U.S. Cl.
CPC .................. *C07J 63/008* (2013.01)

(58) Field of Classification Search
CPC .................................................. C07J 63/008
USPC ......................................................... 552/510
See application file for complete search history.

(56) References Cited

U.S. PATENT DOCUMENTS

2008/0214636 A1  9/2008  Wang et al.
2009/0304712 A1  12/2009  Takeuchi et al.
2011/0190354 A1  8/2011  Takeuchi et al.
2012/0022154 A1  1/2012  Classenhouben et al.
2014/0121166 A1  5/2014  Kielian

FOREIGN PATENT DOCUMENTS

| JP | 2009511511 | 3/2009 |
| JP | 4649549 | 3/2011 |
| WO | 2007088712 | 8/2007 |
| WO | 2010007788 | 1/2010 |
| WO | 2010103046 | 9/2010 |

OTHER PUBLICATIONS

International Search Report, International Application No. PCT/JP2014/080732, dated Dec. 22, 2014.
Kratschmar, et al. "Characterization of Activity and Binding Mode of Glycyrrhetinic Acid Derivatives Inhibiting 11B-Hydroxysteroid Dehydrogenase Type 2"; Journal of Steroid Biochemistry and Molecular Biology, vol. 125, pp. 129-142, 2011.

*Primary Examiner* — Barbara P Badio
(74) *Attorney, Agent, or Firm* — Perman & Green, LLP

(57) ABSTRACT

A novel glycyrrhetinic acid derivative. The glycyrrhetinic acid derivative is represented by the following general formula.

(1)

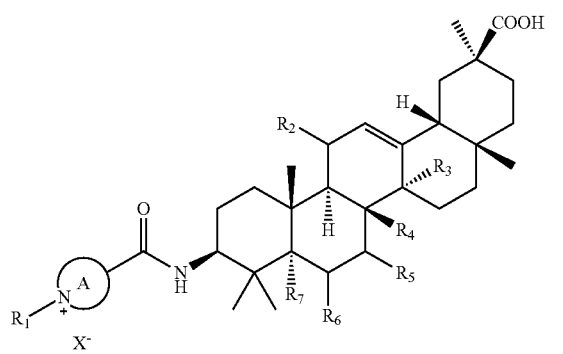

16 Claims, 6 Drawing Sheets

GLYCYRRHETINIC ACID DERIVATIVE AND USE THEREOF

CROSS REFERENCE TO RELATED APPLICATIONS

This application is the National Stage of International Application No. PCT/JP2014/080732, having an International Filing Date of 20 Nov. 2014, which designates the United States of America, and which International Application was published under PCT Article 21(2) as WO Publication No. 2015/076325 A1, and which claims priority from and the benefit of Japanese Application No. 2013-243130, filed 25 Nov. 2013, the disclosures of which are incorporated herein by reference in their entireties.

BACKGROUND

1. Field

The presently disclosed embodiment relates to a novel glycyrrhetinic acid derivative or a pharmaceutically acceptable salt thereof, a pharmaceutical composition comprising the same as an active ingredient, and a method of treatment of a neurological disease using the glycyrrhetinic acid derivative or the pharmaceutically acceptable salt thereof.

2. Brief Description of Related Developments

A gap junction is known as a cell-to-cell contact site on a cell surface. The present inventors have discovered that carbenoxolone (a glycyrrhetinic acid derivative), which is a gap junction inhibitor, inhibits the release of excess glutamate from activated microglia and established that a gap junction inhibitor can be used for treating nervous system diseases.

Furthermore, a gap junction is known to be involved in a variety of transmissions of stimulation such that novel junction inhibitors are useful for various research applications.

SUMMARY

Although carbenoxolone is effective as a gap junction inhibitor, its systemic distribution led to a concern that a mineralocorticoid action in the kidney might cause hypokalemia, edema, and the like. An object of the presently disclosed embodiment is to provide a novel glycyrrhetinic acid derivative which has a more practical gap junction inhibitory action than carbenoxolone.

The present inventors' studies on glycyrrhetinic acid derivatives of carbenoxolone led to the finding that the derivatives obtained by adding, via an amide bond, a heterocyclic salt having 1 to 5 hetero-atoms selected from oxygen, sulfur and nitrogen atoms in replace of the 4-hydroxy-4oxobutanoyl group at position 10, the site connected to the glycoside of the glycyrrhetinic acid skeleton, or a pharmaceutically acceptable salt thereof, increases a pain threshold value and decreases a glutamate concentration in a cerebrospinal fluid, which has led to the completion of the presently disclosed embodiment.

That is, the presently disclosed embodiment provides a glycyrrhetinic acid derivative represented by the following general formula (1) or a pharmaceutically acceptable salt thereof:

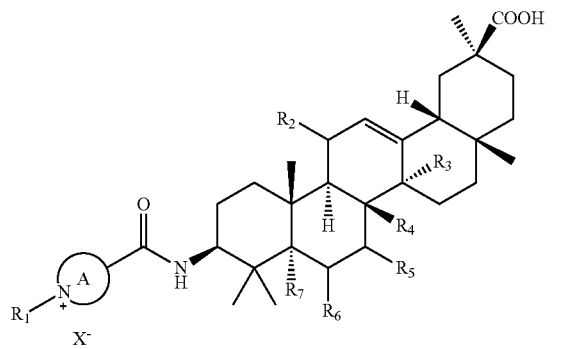

(1)

wherein Ring A represents a heterocyclic ring which may also have a substituent group in addition to R1; R1 represents a linear or branched alkyl group having 1 to 6 carbon atoms; R2 represents a hydroxyl group or a carbonyl group (O=); R3 represents a hydrogen atom, a hydroxyl group or a linear or branched alkyl group having 1 to 4 carbon atoms; R4 represents a hydrogen atom, a hydroxyl group, or a linear or branched alkyl group having 1 to 4 carbon atoms; R5 represents a hydrogen atom, a hydroxyl group, a carbonyl group (O=) or a linear or branched alkyl group having 1 to 4 carbon atoms; R6 represents a hydrogen atom, a hydroxyl group, a carbonyl group (O=), a linear or branched alkyl group having 1 to 4 carbon atoms, or a halogen atom; R7 represents a hydrogen atom or a hydroxyl group; and $X^-$ represents an anion.

In the general formula (1), the Ring A is preferably any one of pyridine, quinoline, isoquinoline, imidazole, oxazole, thiazole, benzoxazole, 2,1-benzisoxazole, benzothiazole or 2,1-benzisothiazole, and particularly pyridine is preferred.

Moreover, the Ring A preferably possesses only R1 as a substituent group.

Further, in the general formula (1), R1 may be an alkyl group having 1 to 4 carbon atoms. Furthermore, R1 may represent a methyl group in the formula (1).

Specific examples of the compounds represented by the general formula (1) include glycyrrhetinic acid derivatives represented by the following chemical formula (2):

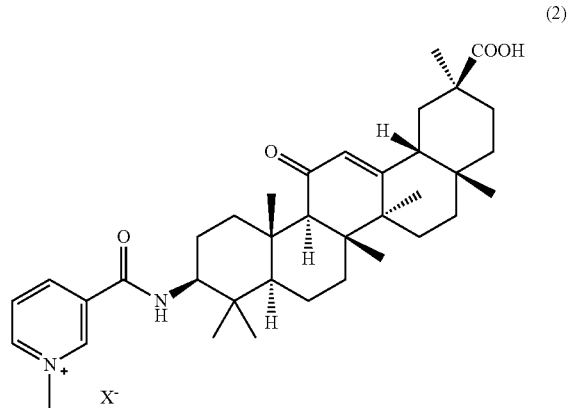

(2)

The presently disclosed embodiment provides a pharmaceutical composition comprising, as an active ingredient, the above-mentioned glycyrrhetinic acid derivative or the pharmaceutically acceptable salt thereof. The pharmaceutical composition of the presently disclosed embodiment can be used for preventing or treating a neurological disease.

Moreover, the presently disclosed embodiment provides a method of treating a mammal afflicted with a neurological disease, the method comprising a step of making available a glycyrrhetinic acid derivative represented by the general formula (1) or a pharmaceutically acceptable salt thereof and a step of administering to the mammal a therapeutically effective amount of the available glycyrrhetinic acid derivative or the pharmaceutically acceptable salt thereof.

The novel method with such constitution is provided for treating mammals afflicted with a neurological disease.

It is preferred in the method that the mammal is a human.

Furthermore, in the compounds represented by the general formula (1) which are used in the therapeutic method, the Ring A is preferably any one of pyridine, quinoline, isoquinoline, imidazole, oxazole, thiazole, benzoxazole, 2,1-benzisoxazole, benzothiazole or 2,1-benzisothiazole, and particularly pyridine is preferred.

Moreover, the Ring A may have only R1 as a substituent group. Further, R1 may be an alkyl group having 1 to 4 carbon atoms. Furthermore, R1 may represent a methyl group in the formula (1).

In addition, the glycyrrhetinic acid derivatives represented by the chemical formula (2) can be mentioned as specific examples of the compounds represented by the general formula (1), and used in the treatment method.

DETAILED DESCRIPTION

Figure 1:
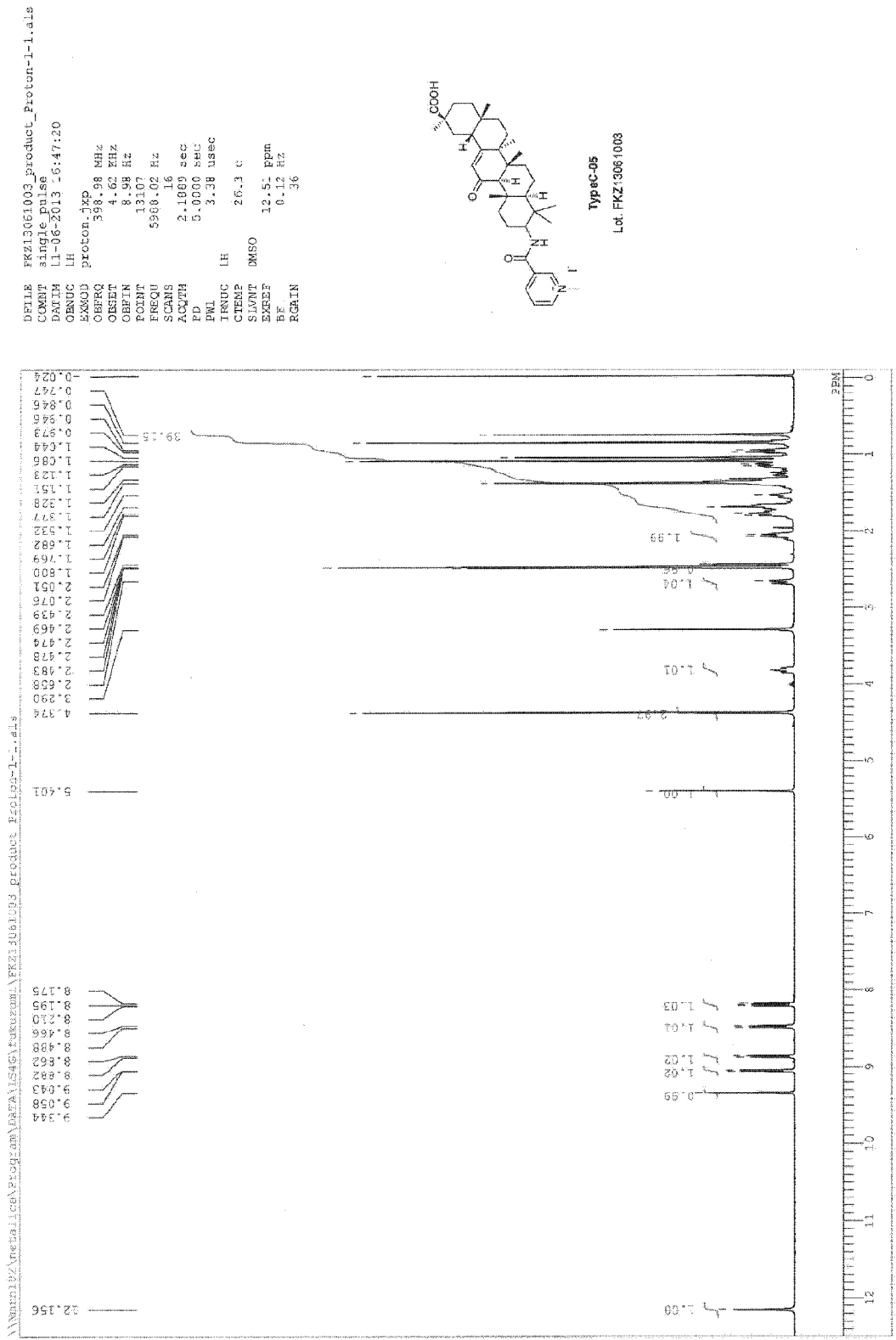
FIG. 1 is a diagram showing the NMR spectrum of Type C-05 synthesized in Example 1.

Here, glutamate release by an activated microglia will be roughly explained. In a microglia which is a kind of glial cell and is in a deactivated state, glutamates produced from α-ketoglutaric acid by an action of transaminase and extracellular glutamates moved into the microglia via glutamic acid transporter are used for normal life supporting activity. Meanwhile, in an activated microglia, it has been made clear that glutamates are produced and released via a route different from a normal one, and specifically in accordance with activation of microglia, glutaminase in the microglia is induced to synthesize glutamates from extracellular glutamine and the synthesized glutamates are released outside the cell from a gap junction hemi-channel.

In brain diseases including diseases accompanying neurodegeneration such as Alzheimer's disease and Parkinson's disease, it has been known that activation of microglia occurs, and also it has been known that when an organic and functional disorder arises in a brain, microglia is activated to give rise to various biological responses.

Therefore, it is possible to inhibit glutamate release by using a gap junction inhibitor inhibiting gap junction in an activated microglia and further to use the gap junction inhibitor for treating nervous system diseases. The novel glycyrrhetinic acid derivative according to the presently disclosed embodiment inhibits the glutamate release from an activated microglia and is capable of treating various neurological diseases.

Specifically the novel glycyrrhetinic acid derivative of the presently disclosed embodiment increases a pain threshold value and decreases a glutamate concentration in a cerebrospinal fluid, and therefore, is useful for preventing or treating a neurodegenerative disease and the like in which neuronal cell death occurs.

The novel glycyrrhetinic acid derivatives of the presently disclosed embodiment can be used as a gap junction inhibitor in themselves and are useful for improving the disease or conditions which can occur as a result of an increase in gap junctions.

The glycyrrhetinic acid derivative of the presently disclosed embodiment will be specifically explained hereinafter.

In the glycyrrhetinic acid derivatives of the presently disclosed embodiment, the Ring A in the compound represented by the general formula (1) is a heterocyclic ring which may have, in addition to R1, one to three identical or different substituent groups. Herein, "heterocyclic ring" means a cyclic compound having 1 to 5 hetero atoms selected from oxygen, sulfur, and nitrogen atoms, preferably pyridine, quinoline, isoquinoline, imidazole, oxazole, thiazole, benzoxazole, 2,1-benzisoxazole, benzothiazole or 2,1-benzisothiazole, more preferably pyridine, quinoline, and isoquinoline. Further, substituent groups which the heterocyclic ring may have are a halogen atom, an alkyl group (the alkyl group may be substituted with a group or groups selected from a halogen atom, a hydroxyl group, an alkoxy group, an amino group, a monoalkylamino group, and a dialkylamino group), a hydroxyl group, an alkoxy group, an amino group (the amino group may be substituted with 1 or 2 groups selected from an alkyl group and an acyl group), a cyano group, a carboxyl group, an alkoxycarbonyl group, an alkanoyl group, an alkenyl group (which may be substituted with an alkoxy group), and the like.

"Halogen atom" means a fluorine, chlorine, iodine or bromine atom; "alkyl" means a linear or branched alkyl having 1 to 6 carbon atoms, preferably 1 to 4 carbon atoms; "alkoxy" means a linear or branched alkoxy having 1 to 6 carbon atoms, preferably 1 to 4 carbon atoms; "alkanoyl" means a linear or branched alkanoyl having 1 to 7 carbon atoms, preferably 2 to 5 carbon atoms; and "alkenyl" means a linear or branched alkenyl having 2 to 6 carbon atoms, preferably 2 to 4 carbon atoms.

The Ring A may have only R1 without having such substituent groups. R1 is preferably an unsubstituted alkyl group. Examples of unsubstituted alkyl groups include methyl, ethyl, propyl, isopropyl, butyl, isobutyl, sec-butyl, tert-butyl, pentyl, isopentyl, neopentyl, tert-pentyl, hexyl, isohexyl, and the like. More preferred alkyl groups are methyl, ethyl, propyl, isopropyl, and butyl; still more preferred is methyl or ethyl; and particularly preferred is methyl.

In addition, there is no particular limitation as to the position at which the Ring A is connected to the glycyrrhetinic acid skeleton. For example, in the case where the Ring A is pyridine and the substituent group is only R1, the ring may be connected to a glycyrrhetinic acid skeleton at any position of the Ring A (pyridine) as shown below.

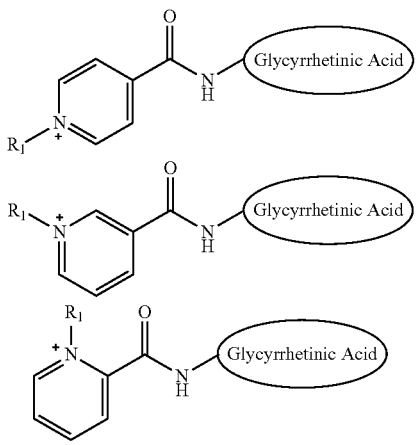

The glycyrrhetinic acid derivative of the presently disclosed embodiment may have various substituent groups in the glycyrrhetinic acid skeleton besides the Ring A, as long as the effect thereof as a gap junction inhibitor is not adversely affected. Specifically, the R2 to R7 in the general formula (1) may be the following substituents, respectively.

For R2, a carbonyl group (O=) or a hydroxyl group; for R3 and R4, a hydrogen atom, a hydroxyl group or a linear or branched alkyl group having 1 to 4 carbon atoms; for R5, a hydrogen atom, a hydroxyl group, a carbonyl group (O=), or a linear or branched alkyl group having 1 to 4 carbon atoms; for R6, a hydrogen atom, a hydroxyl group, a carbonyl group (O=), a linear or branched alkyl group having 1 to 4 carbon atoms or a halogen atom; and for R7, a hydrogen atom or a hydroxyl group.

More preferred are: for R2, a carbonyl group (O=); for R3, a hydrogen atom, a hydroxyl group, a methyl group or an ethyl group; for R4, a hydrogen atom, a methyl group or an ethyl group; for R5, a hydrogen atom, a hydroxyl group or a carbonyl group (O=); for R6, a hydrogen atom or a halogen atom; and for R7, a hydrogen atom or a hydroxyl group.

The glycyrrhetinic acid derivatives of the presently disclosed embodiment may further have substituent groups, in addition to the above-mentioned R2 to R7 in the glycyrrhetinic acid skeleton beside the Ring A. Such substituent groups will not be particularly limited as long as the function thereof as a gap junction inhibitor is not adversely affected, and examples thereof include a halogen atom; an alkyl group (the alkyl group may be substituted with a group or groups selected from a halogen atom, a hydroxyl group, an alkoxy group, an amino group, a monoalkylamino group, and a dialkylamino group); a hydroxyl group, an alkoxy group, an amino group (the amino group may be substituted with one or two groups selected from an alkyl group and an acyl group); a cyano group; a carboxyl group; an alkoxycarbonyl group; an alkenyl group (which may be substituted with an alkoxy group); and the like. Preferred examples among them are an alkyl group, a hydroxyl group, a halogen atom, and the like.

The compounds represented by the following formula (2) are preferable as the glycyrrhetinic acid derivative of the presently disclosed embodiment.

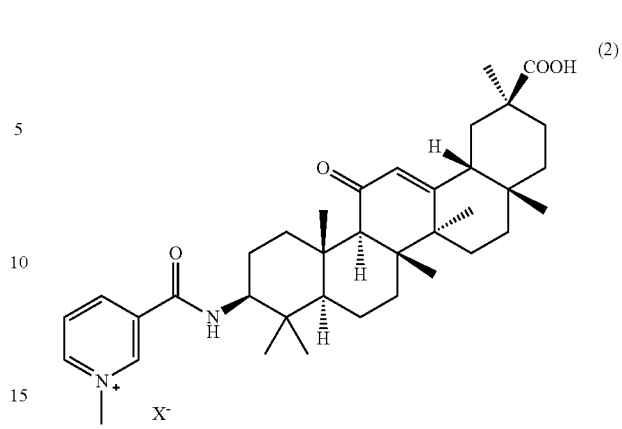

Depending on the substitute group type, the glycyrrhetinic acid derivatives of the presently disclosed embodiment have optical isomers (optically active compounds, diastereomers, and the like) or geometric isomers. Therefore, the glycyrrhetinic acid derivatives of the presently disclosed embodiment include mixtures of these optical isomers or geometric isomers as well as an isomer isolated therefrom.

Further, the $X^-$ in the glycyrrhetinic acid derivatives of the presently disclosed embodiment include an inorganic anion such as chloride ion, bromide ion, iodide ion; and an organic anion such as acetate anion, propionate anion, oxalate anion, and succinate anion, and the like. Preferred are inorganic anions such as iodide ion and the like.

Furthermore, the glycyrrhetinic acid derivatives of the presently disclosed embodiment also include all of the so-called prodrugs that can be metabolized in vivo to the glycyrrhetinic acid derivatives of the presently disclosed embodiment. Listed as groups that form prodrugs with the glycyrrhetinic acid derivatives of the presently disclosed embodiment are those groups described in Prog. Med., 5; 2157-2161 (1985) and those described in "Iyakuhin no Kaihatsu" ("Development of Pharmaceuticals"), vol. 7, Bunshi Sekkei ("Molecular Design"), pp. 163-198, a publication in 1990 by Hirokawa Shoten. Specifically these groups are those that can be converted by hydrolysis, solvolysis or under physiological conditions to HOC (=O)— and the like as in the presently disclosed embodiment: for OH prodrugs, examples thereof include an unsubstituted or substituted lower alkyl-C(=O)O—; an unsubstituted or substituted aryl-C(=O)O—; a ROC(=O)-unsubstituted or substituted lower alkylene-C(=O)O— (where R represents H or a lower alkyl, likewise hereinafter); a ROC(=O)-unsubstituted or substituted lower alkenylene-C(=O)O—; a ROC(=O)-lower alkylene-O-lower alkylene-C(=O)O—, ROC(=O)—C(=O)O—; a ROS(=O)$_2$-unsubstituted or substituted lower alkenylene-C(=O)O—; phthalidyl-O—; 5-methyl-1,3-dioxolene-2-on-4-yl-methyloxy, and the like.

The Method of Producing Glycyrrhetinic Acid Derivatives

The typical method of producing the glycyrrhetinic acid derivatives of the presently disclosed embodiment is explained below.

The glycyrrhetinic acid derivatives of the presently disclosed embodiment can be produced with the application of various synthetic methods in accordance with types of the basic skeleton or substituent group thereof. A representative production method is explained by showing an example for a glycyrrhetinic acid derivative of said general formula (2) where $X^-$ is an iodide ion ($I^-$). A typical production scheme is shown below.

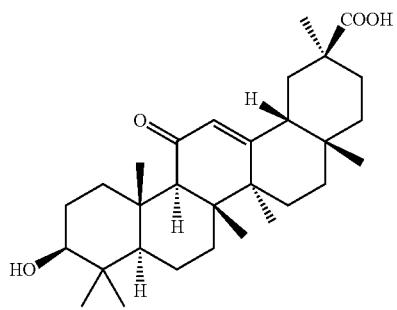

compound 1

→ Jones oxidation, acetone

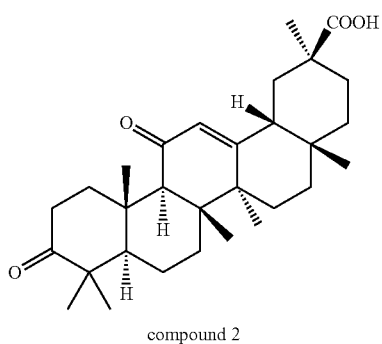

compound 2

→ CH₃I, K₂CO₃, acetone

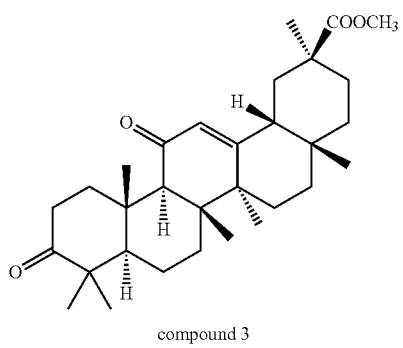

compound 3

→ NH₂OH·HCl, pyridine, Δ

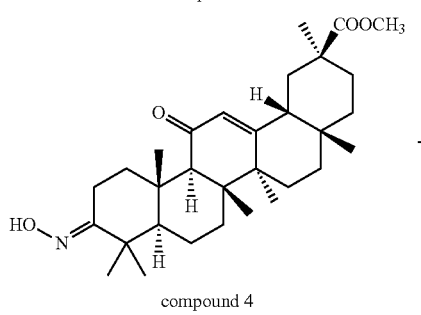

compound 4

→ NaOAc, TiCl₃, BH₃·t-BuNH₂, EtOH

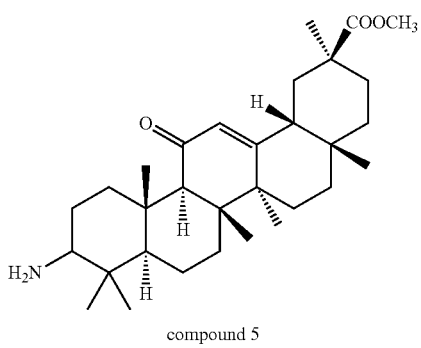

compound 5

→ aq. KOH, Δ, THF, MeOH

-continued

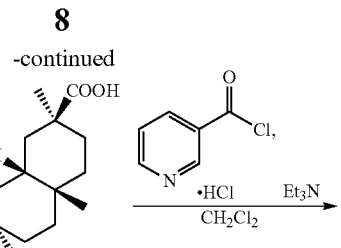

compound 6

→ nicotinoyl chloride·HCl, Et₃N, CH₂Cl₂

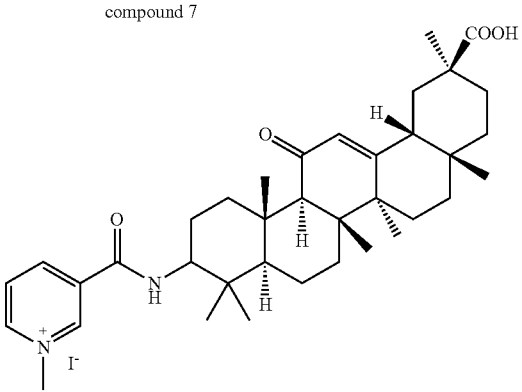

compound 7

→ CH₃I, Δ, CH₃CN—CHCl₃

Type C-05

First, a glycyrrhetinic acid is prepared as a starting material and an amino group is introduced in replace of the hydroxyl group at the site to be connected to the glycoside of the glycyrrhetinic acid skeleton. Subsequently, the glycyrrhetinic acid is reacted with nicotinoyl chloride hydrochloride to form an amide bond, thereby introducing nicotinate, followed by further introduction of an alkyl group to the nitrogen atom of the pyridine ring with methyl iodide or the like.

Typically, the resultant glycyrrhetinic acid derivative of the presently disclosed embodiment is produced and isolated as a pyridinium salt. If the glycyrrhetinic acid derivative of the presently disclosed embodiment is obtained as a free base, however, subjecting it to a salt formation reaction can produce a pyridinium salt thereof.

Further, the raw material compound (starting material) for the glycyrrhetinic acid derivative of the presently disclosed embodiment is available from nature or commercially, and also can be produced from a similar skeletal compound by a synthetic method well known in the art.

Thus, the glycyrrhetinic acid derivatives or pharmaceutically acceptable salts thereof are isolated and purified by applying customary chemical operations such as extraction, concentration, distillation, crystallization, filtration, recrystallization, various types of chromatography, and the like. Further, various isomers can be separated, by selecting the appropriate raw material or by making use of differences in physical or chemical properties among the isomers. For example, optical isomers can be separated into stereochemically pure isomers by selecting an appropriate raw material, or by a racemic resolution (for example by a general method of conversion into a diastereomer salt with a general optically active acid followed by racemic resolution and the like.).

Pharmaceutical Composition

The pharmaceutical composition of the presently disclosed embodiment comprises, as an active ingredient, a glycyrrhetinic acid derivative of the presently disclosed embodiment. The glycyrrhetinic acid derivative of the presently disclosed embodiment is offered as a pharmaceutical composition in various types of preparation forms by applying a variety of conventionally used formulas. The pharmaceutical composition of the presently disclosed embodiment comprises one or more selected from the glycyrrhetinic acid derivatives and pharmaceutically acceptable salts thereof as active ingredients, and, in addition, pharmaceutically acceptable carriers. It is prepared in tablets, powders, fine granules, granules, capsules, pills, liquids, injections, suppositories, ointments, patches, and the like, using carriers, excipients, and other additives which are used conventionally in formulation, and it is administered orally (including sublingual administration) or parenterally including hypodermic injection and intraperitoneal injection.

The formulations, which are pharmaceutical compositions of the presently disclosed embodiment, is produced by well-known methods using additives, such as excipients (for example, organic based excipients, such as sugar derivatives, such as, lactose, sucrose, glucose, mannitol and sorbitol; starch derivatives, such as corn starch, potato starch, α starch and dextrin; cellulose derivatives such as crystalline cellulose; gum arabic; dextran; and pullulan: and inorganic based excipients such as silicate derivatives such as light anhydrous silicic acid, synthetic aluminum silicate, calcium silicate and magnesium meta-silicate aluminate; phosphates such as calcium hydrogen phosphate; carbonates such as calcium carbonate; and sulfates such as calcium sulfate can be listed); lubricants (for example, stearic acid and metal stearate salts such as calcium stearate and magnesium stearate; talc; colloidal silica; waxes such as whale wax, veegum; boric acid; adipic acid; sulfates such as sodium sulfate; glycol; fumaric acid; sodium benzoate; DL leucine; fatty acid sodium salts; lauryl sulfates such as sodium lauryl sulfate and magnesium lauryl sulfate; silicic acids such as anhydrous silicic acid, and silicic acid hydrate; and, the above-mentioned starch derivative can be listed); binders (for example, hydroxypropyl cellulose, hydroxypropyl methyl cellulose, polyvinylpyrrolidone, macrogol, and, compounds similar to the above excipients can be listed); disintegrants (for example, cellulose derivatives such as, hydroxypropyl cellulose having low substitution degree, carboxymethyl cellulose, calcium carboxymethyl cellulose, internally-crosslinked sodium carboxymethyl cellulose; chemically modified starch and celluloses such as carboxymethyl starch, sodium carboxymethyl starch and cross-linked polyvinylpyrrolidone can be listed); stabilizers (para-hydroxy benzoates such as methylparaben and propylparaben; alcohols such as chlorobutanol, benzyl alcohol and phenylethyl alcohol; benzalkonium chloride; phenols such as phenol and cresol; thimerosal; dehydroacetic acid; and, sorbic acid can be listed); flavoring and perfuming agents (for example, commonly used sweeteners, acidulants, flavors, and the like can be listed); diluents and the like.

The dosage of the glycyrrhetinic acid derivative of the presently disclosed embodiment or a pharmaceutically acceptable salt thereof differs depending on the symptoms, age, and the like, and is suitably determined in each case. It can be administered to an adult once or several times a day depending on the symptoms, for example, at a per administration daily lower limit of 0.1 mg (preferably, 1 mg) and a per administration daily upper limit of 1000 mg (preferably 500 mg) for oral administration; and at a per administration daily lower limit of 0.01 mg (preferably, 0.1 mg) and a per administration daily upper limit of 500 mg (preferably 200 mg) for an intravenous administration.

The pharmaceutical composition of the presently disclosed embodiment can be used for preventing, treating, and improving the disease or symptoms caused by an increase in gap junctions, or preventing, treating, and improving the disease or symptoms for which an inhibition of gap junction is effective. For example, it is preferable to be used as a neuronal cell death inhibitor for glutamate-induced excitotoxic neurodegeneration. In addition, it is preferably used for preventing and treating nervous system diseases which involve neuronal cell death due to such excitotoxic neurodegeneration for humans and nonhuman animals such as domesticated animals and pets. The nervous system diseases include, for example, ischemic disorders, inflammatory neurological diseases, and neurodegenerative diseases. The pharmaceutical composition of the presently disclosed embodiment is also useful in reducing neuropathic pain.

Listed for the ischemic disorders are, cerebral stroke, brain hemorrhage, cerebral infarction and cerebrovascular dementia. Listed for the inflammatory neurological disorder are central nervous system inflammatory neurological disorder such as Alzheimer's disease, post-encephalitic syndromes, acute disseminated encephalomyelitis, bacterial meningitis, tuberculous meningitis, fungal meningitis, viral meningitis and post-vaccinal meningitis and the like. Listed for the neurodegenerative disease are, for example, Alzheimer's disease (also an inflammatory neurological disease), head injury, cerebral palsy, Huntington's disease, Pick's disease, Down's syndrome, Parkinson's disease, AIDS encephalopathy, multiple system atrophy, multiple sclerosis (also an inflammatory neurological disease) amyotrophic lateral sclerosis, spinocerebellar degeneration and the like.

In addition, the pharmaceutical composition of the presently disclosed embodiment does not prevent the use thereof with other pharmaceuticals which are effective for neurodegenerative diseases and the like. For example, the combined use thereof with various pharmaceuticals used for ischemic disorders, inflammatory neurological diseases, and neurodegenerative diseases is not barred. For the Alzheimer's disease, examples thereof include donepezil, memantine, rivastigmine, galanthamine, and the like; for the multiple sclerosis, examples thereof include interferon, glucocorticosteroid, anticonvulsant drugs, an immunosuppressant and the like; for the Parkinson's disease, examples thereof include dopamine, anticholinergic agent, a dopamine release inhibitor (amantadine); dopamine receptor stimulant (ergot or non-ergot alkaloid); dopamine breakdown inhibitor (Selegilene) and the like; for the spinocerebellar degeneration, examples thereof include protirelin tartrate, taltirelin hydrate; for the amyotrophic lateral sclerosis, examples thereof include riluzole and the like.

Comparison with Other Glycyrrhetinic Acid Derivatives

The present inventors have also achieved synthesis of a glycyrrhetinic acid derivative that is different from the glycyrrhetinic acid derivative of the presently disclosed embodiment (JP 4649549 B). Similar to the glycyrrhetinic acid derivative of the presently disclosed embodiment, the glycyrrhetinic acid derivative of this disclosed embodiment ("compound B" in the disclosed embodiment, hereinafter referred to as "compound B") inhibits glutamate release from an activated microglia by inhibiting gap junction and neuronal cell death, and can be a therapeutic agent of various neurological diseases.

Comparing the presence of intracerebral migration in the case where the glycyrrhetinic acid derivative of the presently disclosed embodiment and the compound B are respectively administered via various paths, it has been clarified that both the glycyrrhetinic acid derivative of the presently disclosed embodiment and the compound B are delivered into brain via an intraarterial injection and an intravenous injection. In the case where an intraperitoneal injection is used, the both glycyrrhetinic acid derivative of the presently disclosed embodiment and the compound B reach a central nervous system and exert a medicinal effect in experiments using model mice. However, it has been clarified that in the case where the compound B is injected hypodermically into model mice, it does not delivered into brain. On the other hand, it has been clarified that the glycyrrhetinic acid derivative of the presently disclosed embodiment is delivered into brain even in the case where it is injected hypodermically (see Examples described below). While the compound B and the glycyrrhetinic acid derivative of the presently disclosed embodiment have the similar structures, the mechanisms thereof in migration into brain cells are considered to be different and this is considered to be because lipid solubility (Log D) of the glycyrrhetinic acid derivative of the presently disclosed embodiment is slightly lower than that of the compound B (compound B=4.28, the glycyrrhetinic acid derivative of the presently disclosed embodiment (compound no. 37 in Examples described below)=2.94). In this respect, the presently disclosed embodiment has a significant effect.

The presently disclosed embodiment is explained specifically hereinafter with examples, but the disclosed embodiment is not limited to these examples.

EXAMPLE 1

Synthesis of the Glycyrrhetinic Acid Derivatives of the Presently Disclosed Embodiment The glycyrrhetinic acid derivative (hereinafter also referred to as Type C-05), which is the compound of the formula (2) having $X^-$ of iodine ion ($I^-$), of the presently disclosed embodiment was synthesized according to the following scheme:

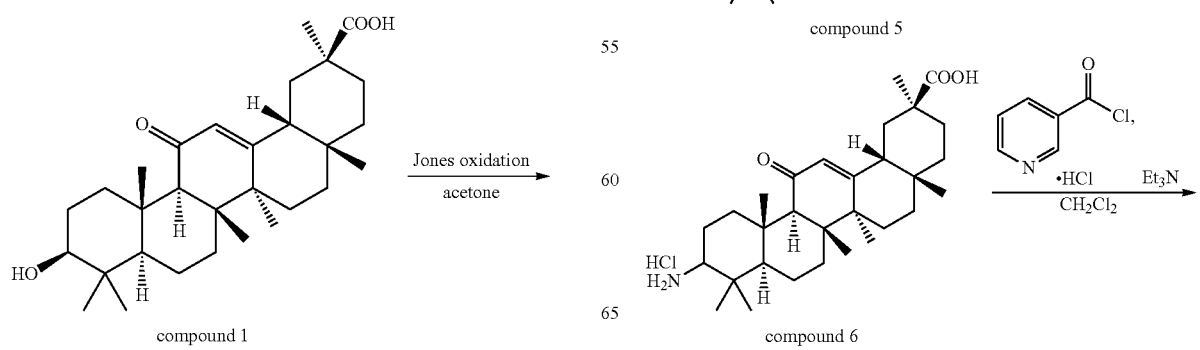

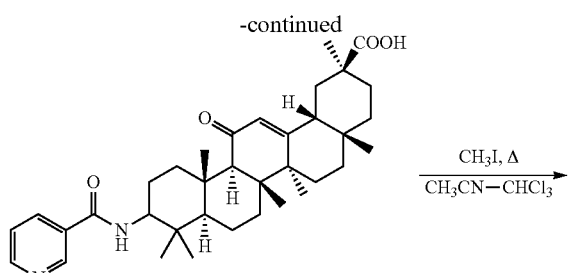

compound 7

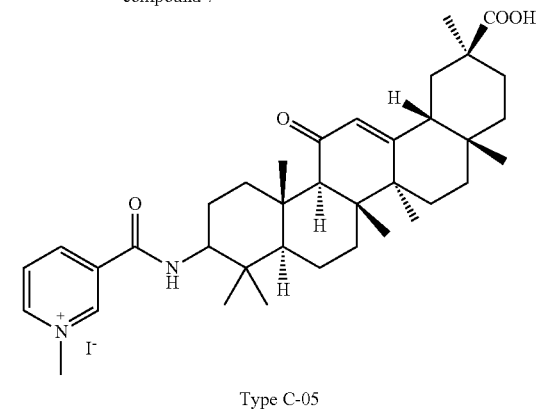

Type C-05

Each step will be explained below.
(1) First Step

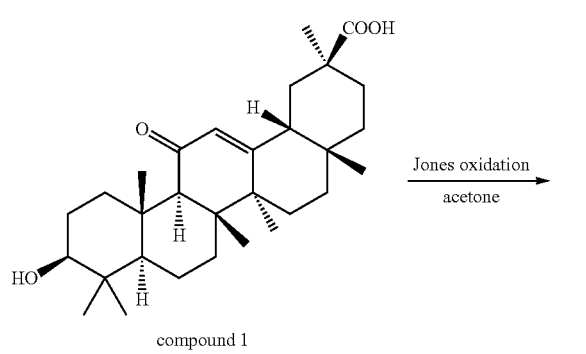

compound 1

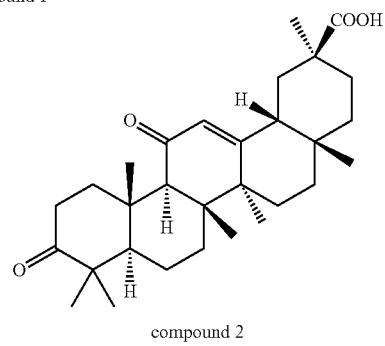

compound 2

After dissolving glycyrrhetinic acid (Compound 1, 327 g, 694 mmol) into acetone (6.5 L), Jones reagent (306 mL, 765 mmol) was slowly added thereto under ice cooling, followed by stirring for two hours at the same temperature. Then, additional Jones reagent (30 mL) was added, followed by stirring for additional one and a half hours at the same temperature. The resultant solution was poured into ice-cooled water (6.0 L), and chloroform (6.0 L) was added thereto, followed by stirring for a while and then filtration with a filter paper. A solid on a funnel was washed with chloroform. After the filtrate was separated, the organic layer was washed with water (6.0 L) three times and then dried over anhydrous sodium sulfate. After the filtration, the filtrate was concentrated under reduced pressure to obtain a target compound (Compound 2, 302 g, 645 mmol, a white solid). The yield was 93%.

(2) Second Step

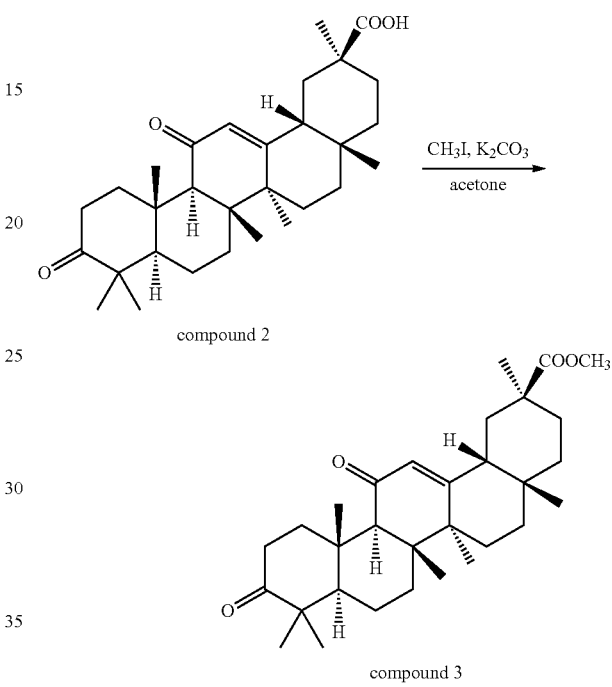

compound 2 compound 3

After dissolving a keton compound (Compound 2, 302 g, 645 mmol) into acetone (6 L), potassium carbonate (134 g, 968 mmol) was added thereto, and methyl iodide (60 mL, 968 mmol) was slowly added, followed by stirring overnight at a room temperature. The resultant solution was poured into water (10 L), and chloroform (8 L) was added, followed by stirring and the separation. The organic layer was dried over anhydrous sodium sulfate, followed by filtration, and then the filtrate was concentrated under reduced pressure to obtain a target compound (Compound 3, 304 g, 630 mmol). The yield was 98%.

(3) Third Step

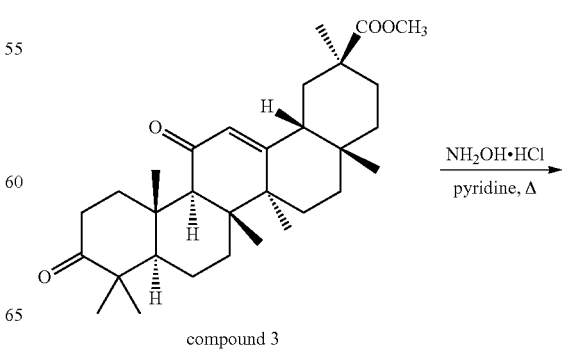

compound 3

-continued

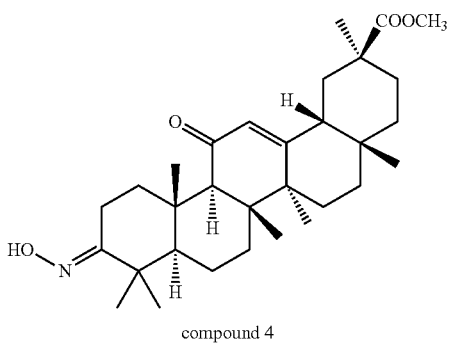

compound 4

In a 2 liter flask were poured a keton compound (Compound 3, 80.0 g, 166 mmol) and pyridine (400 ml). The powder was not fully dissolved. Hydroxylamine hydrochloride (58 g, 834 mmol, 5 eq) was added thereto while stirring. After stirring for two hours at an internal temperature of 40° C., the disappearance of the starting material was confirmed. The solvent was distilled off under reduced pressure, and 3M hydrochloric acid was added under ice cooling. After extraction with chloroform, washing with a saturated saline solution, and then drying over anhydrous sodium sulfate, the solvent was distilled off under reduced pressure. The obtained compound (Compound 4, 81.6 g, 164 mmol, a white powder) was used as it was for the next reaction. The yield was 99%.

(4) Fourth Step

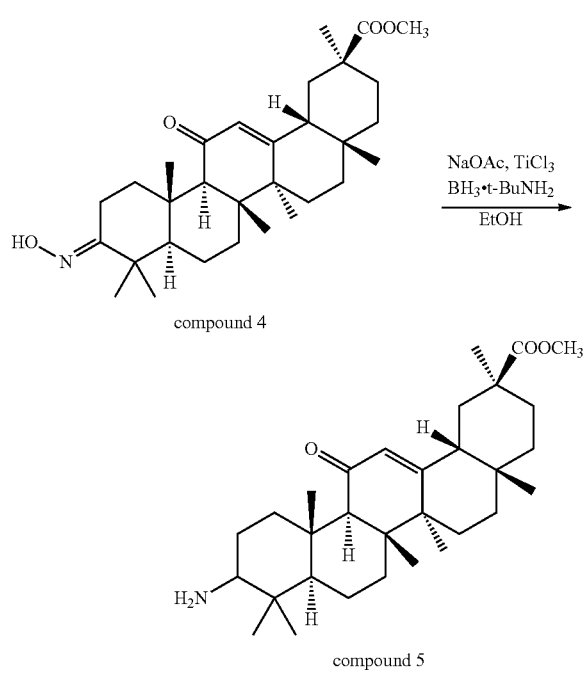

Preparation of TiCl$_3$ Solution (12% TiCl$_3$, 5% HCl)

Concentrated hydrochloric acid (104 mL) was added to water (260 mL) and 376 mL of TiCl$_3$ (22%) was added under ice cooling. While bubbling and stirring argon gas, sodium acetate (215 g) was added, followed by dilution with water (160 mL).

In a 5 liter flask, an oxime compound (Compound 4, 81.6 g, 164 mmol) was dissolved in 1600 mL of ethanol. Borane (35.6 g, 410 mmol) was added thereto, followed by ice cooling. While bubbling argon gas, separately prepared TiCl$_3$ solution (12% TiCl$_3$, 5% HCl, the solution prepared above) was added dropwise over four hours, followed by elevation of temperature up to a room temperature over 15 hours. Then, a saturated saline solution (300 mL) was added, and the resultant solid was removed by filtering, followed by washing with methanol. The solvent was distilled off under reduced pressure till it was reduced to 2 L, followed by separation with chloroform (2.0 L). The organic layer was washed with saturated sodium bicarbonate (200 mL) and dried over anhydrous sodium sulfate, and the solvent was distilled off under reduced pressure. The obtained solid (Compound 5, 51.9 g, 1.07 mmol, a white powder) was used for the next reaction without being purified. The yield was 66%.

(5) Fifth Step

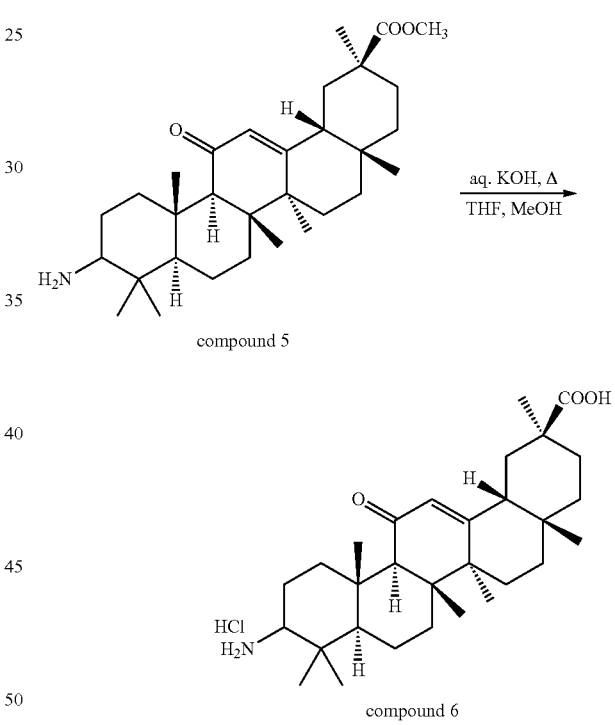

An amine compound (Compound 5, 51.9 g, 107 mmol) was dissolved into THF (900 mL) and MeOH (900 ml). And thereto was added slowly an alkaline aqueous solution prepared by dissolving potassium hydroxide (180 g, 3.21 mol) in water (450 mL). After stirring for one hour at an internal temperature of 60° C., the solvent was distilled off under reduced pressure. An aqueous solution of saturated ammonium chloride was added and a precipitated white powder was filtered and washed with water. The white powder was dried under reduce pressure, and then suspended and washed with ethyl acetate/methanol=9/1 (500 ml) to obtain a target compound (Compound 6, 38.4 g, 75.9 mmol, a white powder). The yield was 77%.

(6) Sixth Step

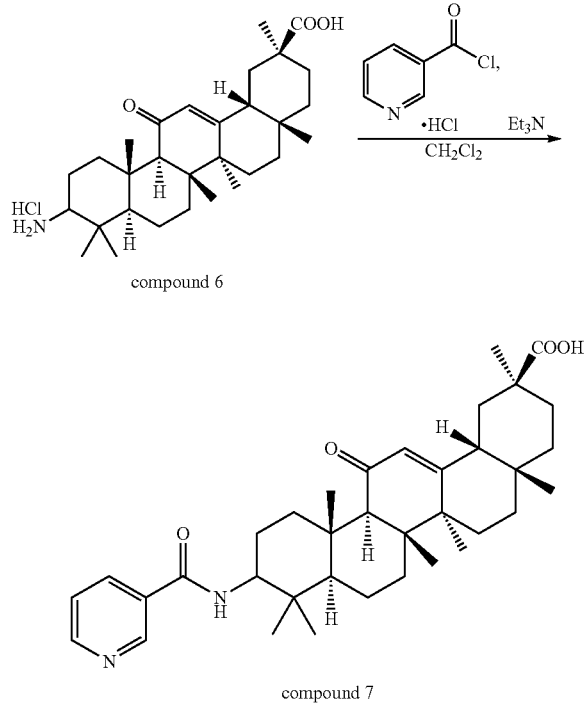

compound 6

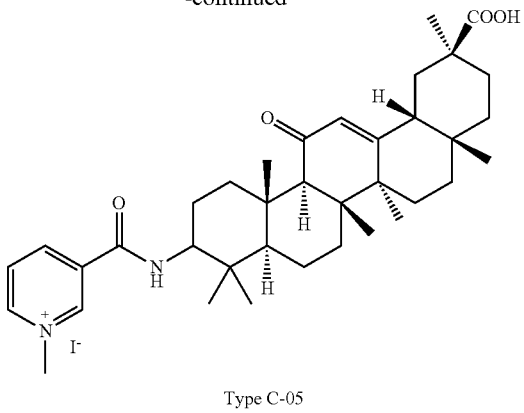

Type C-05

Figure 2:
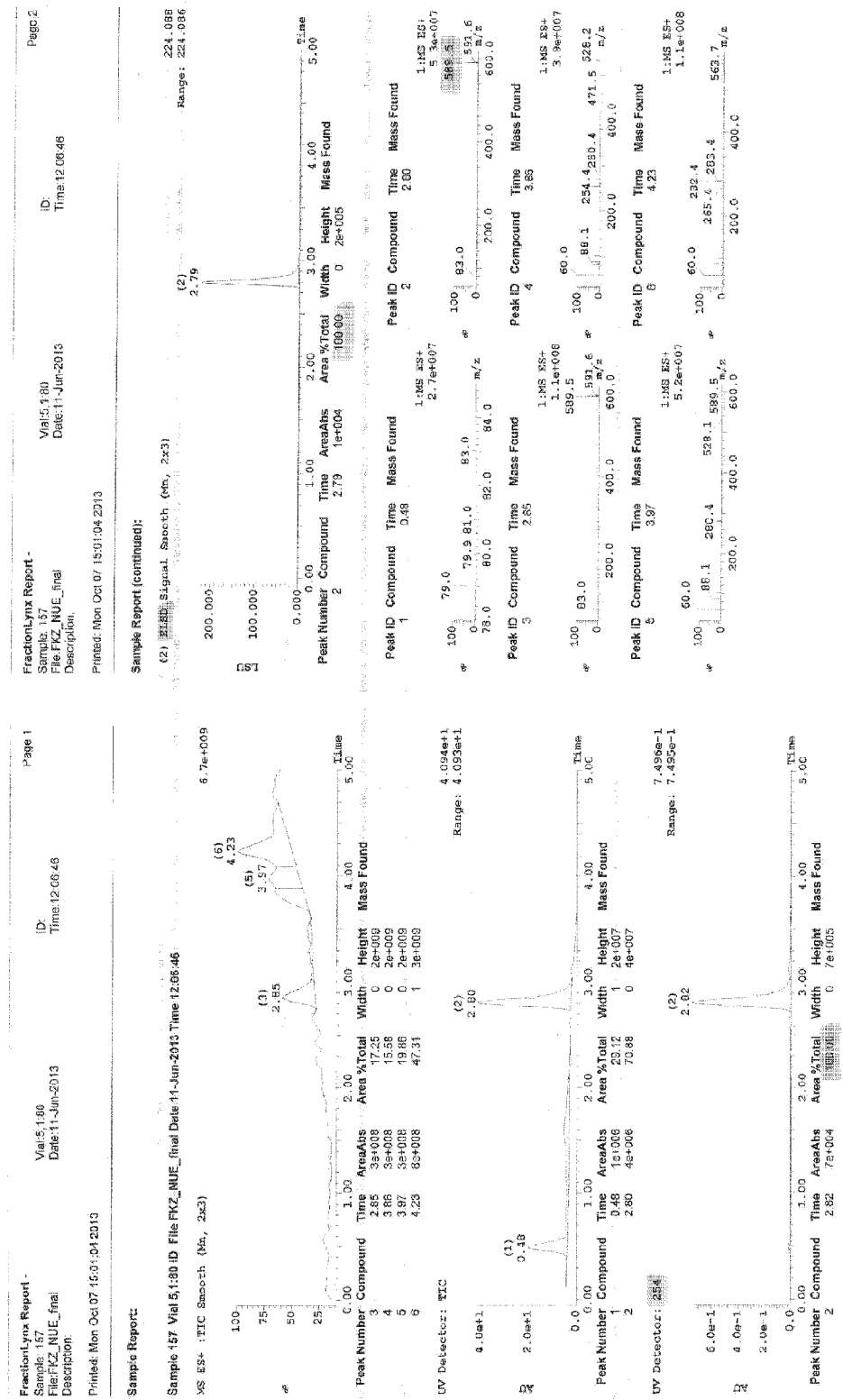
FIG. 2 is a diagram showing the LC-MS spectrum of Type C-05 synthesized in Example 1.

In a 500 mL flask was put nicotinic acid derivative (Compound 7, 5.0 g, 8.70 mmol, 1.0 eq) which was then dissolved into acetonitrile (50 mL) and chloroform (50 mL), and methyl iodide (1.1 mL, 17.7 mmol, 2 eq) was added thereto. The reaction solution was heated and refluxed for 15 hours, and then was slowly cooled with stirring. The obtained precipitate was filtered and washed with acetonitrile and chloroform (1/1), and after drying under reduced pressure, a crude material of a target product (Type C-05, 1.99 g, a yellow powder) was obtained. The above reaction was conducted in the same manner with the scales of nicotinic acid derivative (Compound 7) of 19.3 g, 15.0 g, and 9.1 g, respectively to obtain crude materials of a target product (Type C-05, 25.7 g, a yellow powder). To the total amount of the crude materials (27.7 g) including the crude material (1.99 g) obtained by the above reaction was added ethyl acetate (an appropriate amount), followed by suspension and washing to obtain Type C-05 (27.1 g, 37.8 mmol, a light yellow solid). The total yield was 49%. NMR spectrum of the obtained Type C-05 is shown in FIG. 1. Also, LC-MS spectrum is shown in FIG. 2.

compound 7

In a 2 liter flask was poured an amine-carboxylic acid compound (Compound 6, 38.4 g, 79.4 mmol), and methylene chloride (530 mL) and triethylamine (44.0 mL, 317 mmol, 4 eq) were added thereto. Under ice cooling, nicotinoyl chloride hydrochloride (21.2 g, 119 mmol, 1.5 eq) was added while stirring, followed by stirring for 30 minutes under ice cooling and for 30 minutes at a room temperature. An aqueous solution of saturated ammonium chloride (200 mL) was added thereto, and water layer was extracted with chloroform (100 mL) twice. An organic later was washed with a saturated saline solution, and then dried over anhydrous sodium sulfate, and the solvent was distilled off under reduced pressure. The obtained solid was suspended in and washed with ethyl acetate/heptane=1/1 (500 mL), and after drying under reduced pressure, a target compound (Compound 7, 39.8 g, 69.2 mmol, a white powder) was obtained. The yield was 87%.

(7) Seventh Step

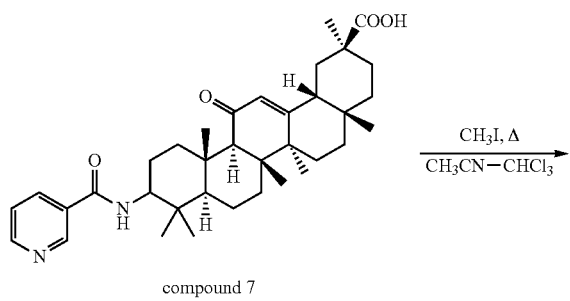

compound 7

EXAMPLE 2

Pain Behavior Test (Mechanical Allodynia)

Chronic pain was caused by performing a chronic constriction injury (CCI) operation of sciatic nerve on a hind leg of a C57BL/6J mouse (8 week old, n=4 in each group). Threshold values of mechanical strength which indicated avoidance behavior were recorded by pressing a von Frey hair against the foot pad of the mouse's hind leg (from the previous day of the CCI operation to the 14th day after the operation).

Regarding drugs, the below drugs were administered once a day from the 7th day to the 14th day after the operation, and the therapeutic effects were studied. In this example, "Compound No. 37" is a compound represented by the above formula (2).

Figure 3:
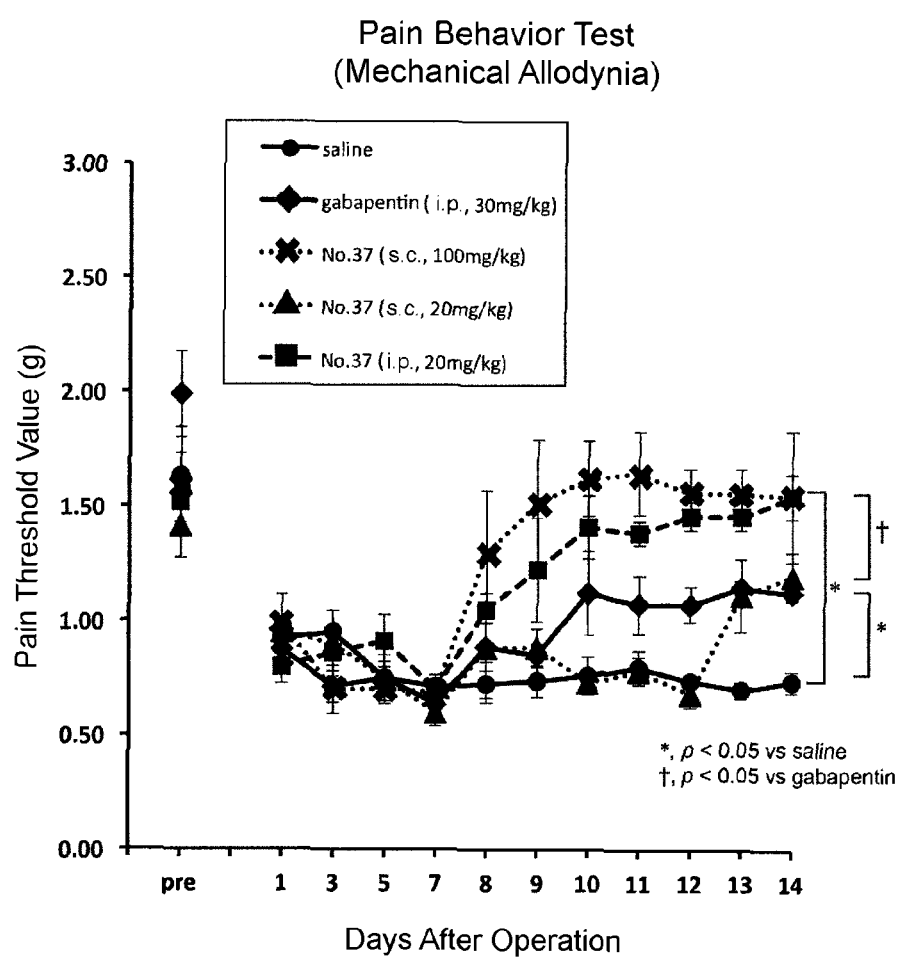
FIG. 3 is a diagram showing the time course change in the pain threshold value in the pain behavior test in C57BL/6J mice. Herein the * represents $p<0.05$ vs physiological saline and the † represents $p<0.05$ vs Gabapentin.

Control: the same volume of physiological saline
    Gabapentin: 30 mg/kg, intraperitoneal administration
    Compound No. 37: 100 mg/kg, subcutaneous administration
    Compound No. 37: 20 mg/kg, subcutaneous administration
    Compound No. 37: 20 mg/kg, intraperitoneal administration As shown in FIG. 3, each test group began varying from the 8th day of the observation after the operation, and, compared to Gabapentin group, significant increases of pain threshold values were observed in the group of subcutaneous administration with 100 mg/kg of Compound No. 37 and the group of intraperitoneal administration with 20 mg/kg of Compound No. 37. Especially in the intraperitoneal administration group, an increase of pain threshold value was observed at a concentration lower than Gabapentin.

EXAMPLE 3

Cerebrospinal Fluid Glutamate Concentration Determination

On the 14th day after the CCI operation, cerebrospinal fluid were collected from the foramen magnum of the above-mentioned mice, and the glutamate concentration was measured quantitatively with HPLC.

Figure 4:
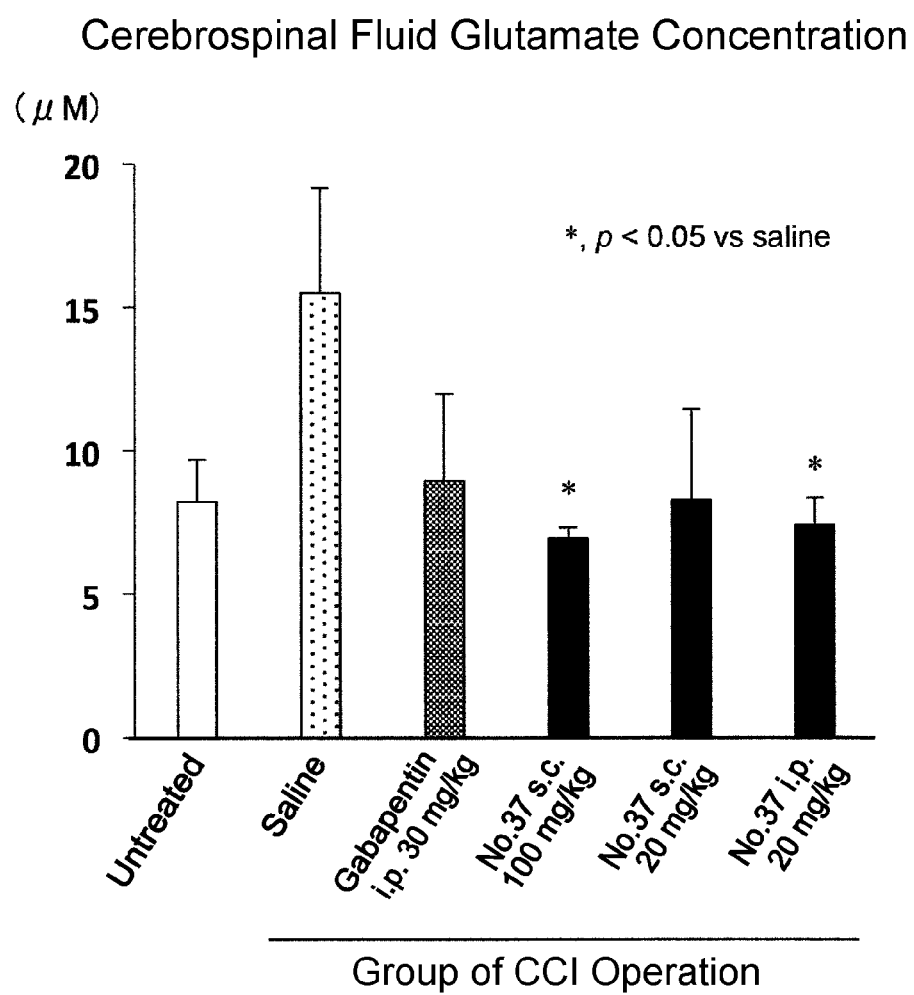
FIG. 4 is a diagram showing the glutamate concentration in a cerebrospinal fluid in C57BL/6J mice.

As shown in FIG. 4, in any of the groups of Compound No. 37 (100 mg/kg, subcutaneous administration), Compound No. 37 (20 mg/kg, subcutaneous administration), and Compound No. 37 (20 mg/kg, intraperitoneal administration), a decrease of the glutamate concentration in the cerebrospinal fluid, which was equal to or more than that shown in Gabapentin group, was observed.

From the above, it was found that the compound of the above formula (2) decreases the glutamate concentration in cerebrospinal fluid and thereby increases pain threshold value. From this, it was speculated that the compound of the formula (2) inhibits neuronal cell death.

EXAMPLE 4

LD50 Test

LD50 (lethal dose 50%) of the glycyrrhetinic acid derivative (the compound of the above formula (2)) of the disclosed embodiment and LD50 of carbenoxolone were compared. The result showed that LD50 of the glycyrrhetinic acid derivative of the disclosed embodiment was >5000 mg/kg (not shown in figures), while LD50 of carbenoxolone was 100 mg/kg. From this, it can be seen that the glycyrrhetinic acid derivative of the disclosed embodiment has a higher maximum tolerated dose compared to carbenoxolone and is superior to conventional gap junction inhibitors from the perspective of safety as well.

EXAMPLE 5

Checking the Survival Extension Effect in ALS Acute-Onset Model Mice

The assessment of drug efficacy was conducted using, as an animal model of neurodegenerative diseases, the human superoxide dismutase 1 (SOD1) G93A mutant transgenic mice, which are widely used as an acute-onset model of amyotrophic lateral sclerosis (ALS).

Starting at 7-8 weeks of age, which is considered to be an early ALS onset period, the mice were intraperitoneally administered with 20 mg/kg body weight of the glycyrrhetinic acid derivative of the disclosed embodiment (Compound No. 37 group) or the same volume of physiological saline (saline group) three times a week.

The survival analysis was performed using the Kaplan-Meier method. The results are shown in FIG. 5.

Figure 5:
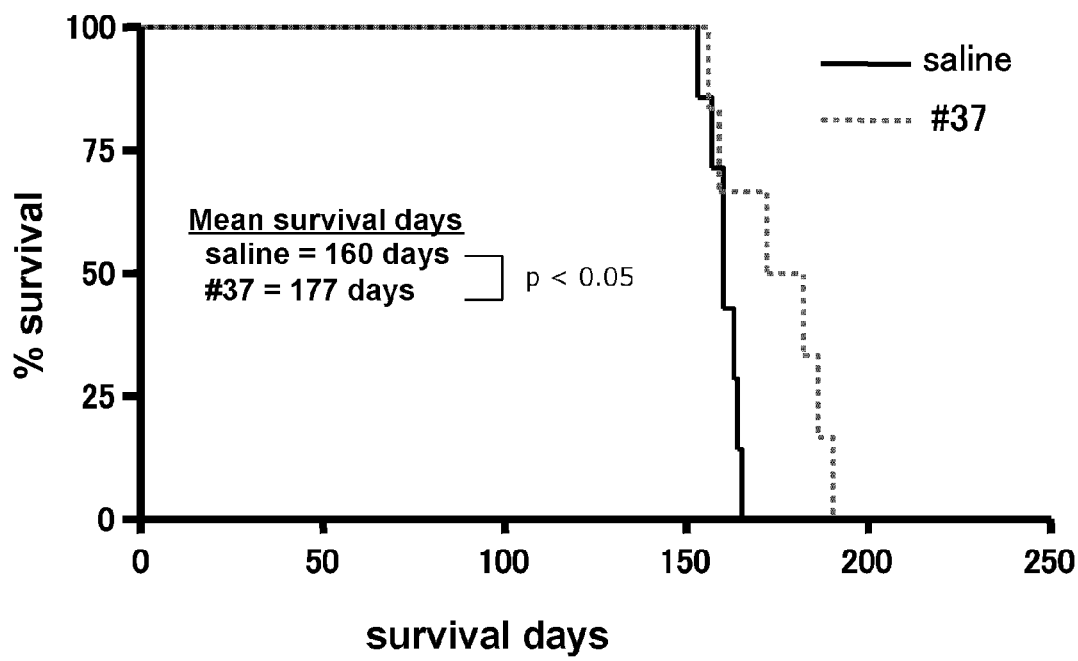
FIG. 5 is a diagram showing the result of survival extension effect of ALS acute-onset model mice in accordance with the administration of the glycyrrhetinic acid derivative of the presently disclosed embodiment.

As shown in FIG. 5, the group of the glycyrrhetinic acid derivative of the disclosed embodiment administration showed on average an effect of extending survival by about 17 days ($p<0.05$). This value is considered to be a very good survival extension effect for this model mouse.

EXAMPLE 6

Checking the Survival Extension Effect in Alzheimer's Disease Model Mice

The assessment of drug efficacy of the glycyrrhetinic acid derivative of the disclosed embodiment (Compound No. 37 group) was conducted using, as an animal model of neurodegenerative diseases, the human amyloid $\beta$1-42 peptide (A$\beta$) intraventricularly injected mice (Doi et al., Am J Pathol. 175 (5): 2121-32, 2009), which are widely used as an Alzheimer's disease model.

The mice were intraventricularly injected with 300 pmol/3 μl of A$\beta$, and from the day of the injection, they were intraperitoneally administered with 20 mg/kg body weight of the glycyrrhetinic acid derivative (Compound No. 37 group) of the disclosed embodiment or the same volume of physiological saline (vehicle group) three times a week. For control group was used wild type mouse (G57BL/6J) of the same age. Behavioral analysis was performed using the following fear conditioned learning test.

Fear Conditioned Learning Test

Figure 6:
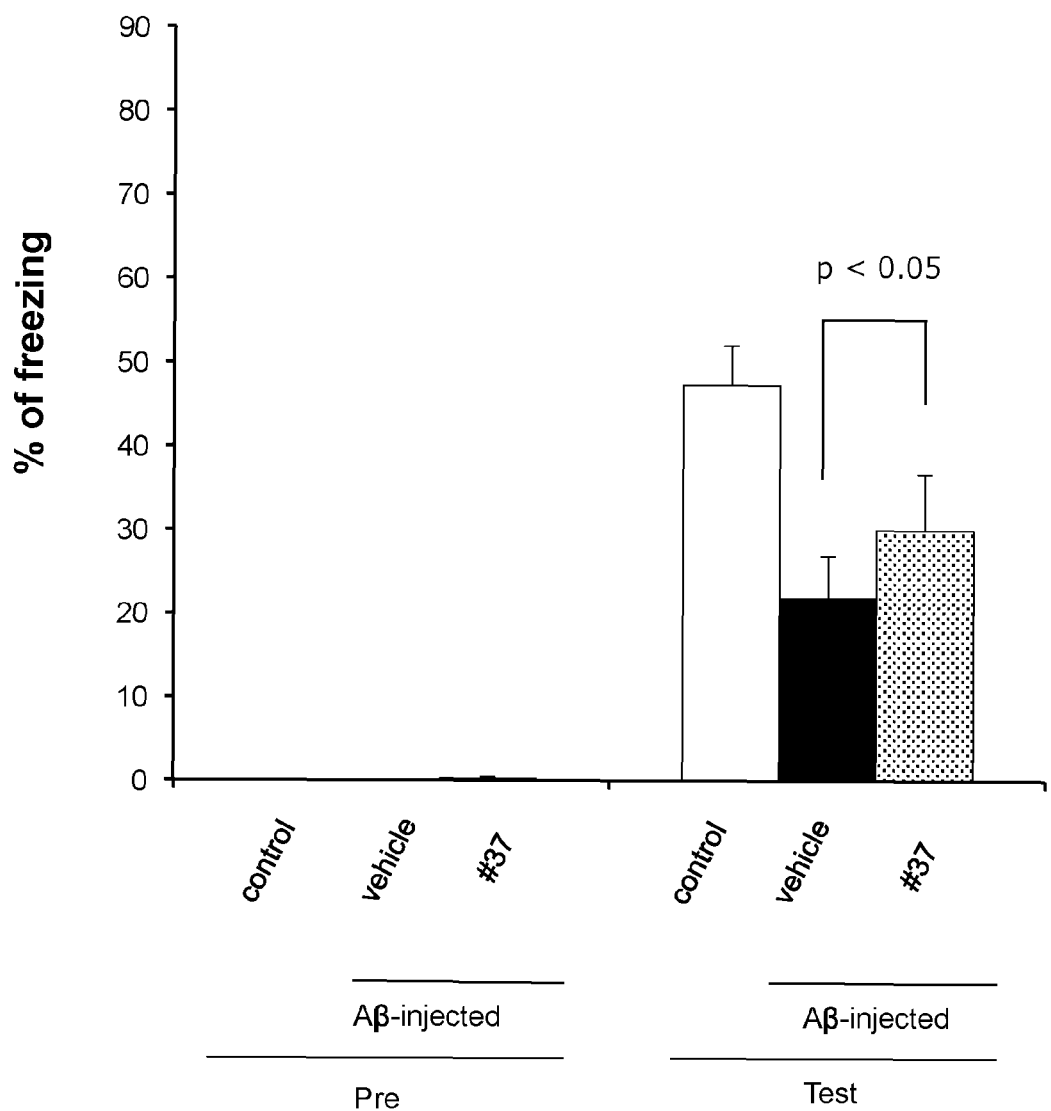
FIG. 6 is a diagram showing the memory disorder improvement effect of the glycyrrhetinic acid derivative of the presently disclosed embodiment on Alzheimer's disease model mice.

Associative learning was assessed using a fear conditioned learning test (Mouri et al., FASEB J. 21, 2135-2148, 2007; Nagai et al., FASEB J. 17, 50-52, and 2003). The mice were placed in a transparent acrylic cage with a stainless steel grid installed therein and were subjected to a 20 second tone stimulus (80 dB) and to an electric stimulus (0.6 mA) in the last 5 seconds. A set of this combination stimulus was repeated 4 times with 15 second intervals, thereby causing fear conditioning. A contextual dependency test and a tone stimulus dependency test were carried out 24 hours after the fear conditioning. For the former, mice were placed in the white acrylic cage with a grid where the fear conditioning took place to determine their freezing behavior for two minutes in a context of giving no tone and no electric stimuli. For the latter, mice were placed in a black acrylic cage having wood chips on the floor thereof, to determine their freezing behavior for 1 minute when given a continuous tone stimulus. The results were expressed respectively in terms of a percentage (%) of the freezing behavior time relative to the total time for determination. The results are shown in FIG. 6.

The group of the glycyrrhetinic acid derivative of the disclosed embodiment administration group significantly moderated the observed reduction in freezing behavior time in the contextual dependency test in the case of the group of A$\beta$ intraventricularly injected mice with administered physiological saline, and significant improvement effects in memory disorders were shown ($p<0.05$).

What is claimed is:

1. A qlycyrrhetinic acid derivative represented by the following general formula (1) or a pharmaceutically acceptable salt thereof:

(1)

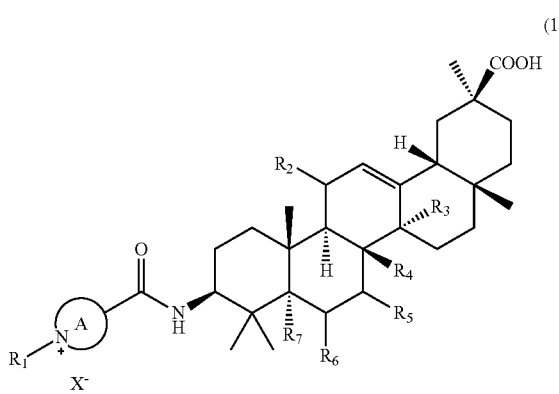

wherein Ring A represents a heterocyclic ring which may also have a substituent group in addition to R1;
R1 represents a linear or branched $C_{1-6}$ alkyl group;
R2 represents a hydroxyl group or a carbonyl group (O=);
R3 represents a hydrogen atom, a hydroxyl group or a linear or branched $C_{1-4}$ alkyl group;
R4 represents a hydrogen atom, a hydroxyl group, or a linear or branched $C_{1-4}$ alkyl group;
R5 represents a hydrogen atom, a hydroxyl group, carbonyl group (O=) or a linear or branched $C_{1-4}$ alkyl group;
R6 represents a hydrogen atom, a hydroxyl group, a carbonyl group (O=), a linear or branched $C_{1-4}$ alkyl group, or a halogen. atom;
R7 represents hydrogen atom or a hydroxyl group; and
$X^-$ represents an anion.

2. The glycyrrhetinic acid derivative of claim 1, wherein in the general formula (1), the Ring A is any one of pyridine, quinoline, isoquinoline, imidazole, oxazole, thiazole, benzoxazole, 2,1-benzisoxazole, benzothiazole or 2,1-benzisothiazole.

3. The glycyrrhetinic acid derivative of claim 2, wherein in the general formula (1), the Ring A has only R1 as a substituent group.

4. The glycyrrhetinic acid derivative of claim 3, wherein in the general formula (1), R1 represents a methyl group.

5. The glycyrrhetinic acid derivative of claim 4, wherein in the general formula (1), the Ring A is pyridine.

6. The glycyrrhetinic acid derivative of claim 5 represented by the following chemical formula:

(2)

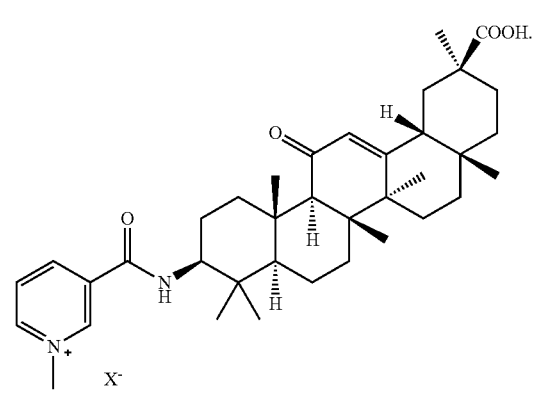

7. A pharmaceutical composition comprising, as an active ingredient, the glycvrrhetinic acid derivative of claim 1.

8. A method of treating a mammal afflicted with a neurological disease selected from the group consisting of neuropathic pain, Alzheimer's disease, amyotrophic lateral sclerosis and Parkinson's disease, the method comprising:
a step of making available a therapeutically effective amount of a glycyrrhetinic acid derivative represented by general formula (1) or a pharmaceutically acceptable salt thereof:

(1)

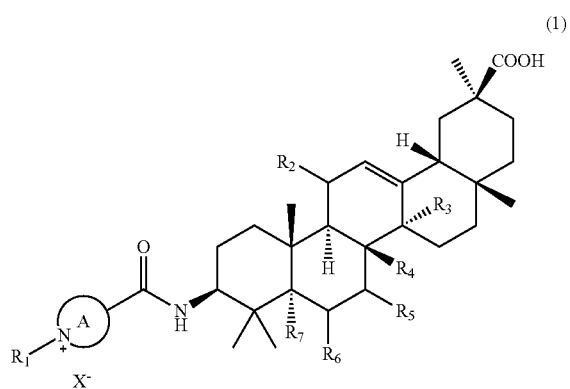

wherein Ring A represents a heterocyclic ring which may also have a substituent group in addition to R1;
R1 represents a linear or branched $C_{1-6}$ alkyl group;
R2 represents a hydroxyl group or a carbonyl group (O=);
R3 represents a hydrogen atom, a hydroxyl group or a linear or branched $C_{1-4}$ alkyl group;
R4 represents a hydrogen atom, a hydroxyl group, or a linear or branched $C_{1-4}$ alkyl group;
R5 represents a hydrogen atom, a hydroxyl group, a carbonyl group (O=) or a linear or branched $C_{1-4}$ alkyl group;
R6 represents a hydrogen atom, a hydroxyl group, a carbonyl group (O=), a linear or branched $C_{1-4}$ alkyl group, or a halogen atom;
R7 represents a hydrogen atom or a hydroxyl group; and
$X^-$ represents an anion, and
a step of administering to the mammal a therapeutically effective amount of the available glycyrrhetinic acid derivative or the pharmaceutically acceptable salt thereof.

9. The method of claim 8, wherein the mammal is a human.

10. The method of claim 8, wherein the Ring A the general formula (1) is any one of pyridine, quinoline, isoquinoline, imidazole, oxazole, thiazole, benzoxazole, 2,1-benzisoxazole, benzothiazole or 2,1-benzisothiazole.

11. The method of claim 10, wherein the Ring A the general formula (1) has only R1 as a substituent group thereof.

12. The method of claim 11, wherein R1 in the general formula (1) represents a methyl group.

13. The method of claim 12, wherein Ring A in the general formula (1) is pyridine.

14. The method claim 13, wherein a compound represented by the following chemical formula is used as the glycyrrhetinic acid derivative or the pharmaceutically acceptable salt thereof:

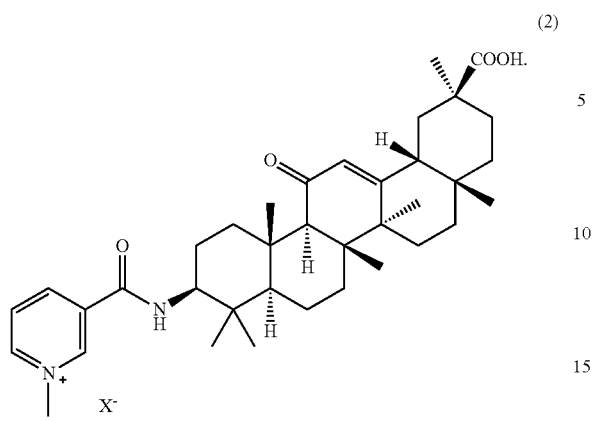
(2)
15. The pharmaceutical composition of claim 7, wherein the composition is in the form of hypodermic injection.
16. The method of claim 8, wherein the glycyrrhetinic acid derivative or the pharmaceutically acceptable salt thereof is injected hypodermically.
* * * * *

UNITED STATES PATENT AND TRADEMARK OFFICE
CERTIFICATE OF CORRECTION

PATENT NO. : 9,796,751 B2  
APPLICATION NO. : 15/038970  
DATED : October 24, 2017  
INVENTOR(S) : Takeuchi et al.

Page 1 of 1

It is certified that error appears in the above-identified patent and that said Letters Patent is hereby corrected as shown below:

In the Claims

Column 21, Claim 1, Line 31, delete the "." after "halogen".

Column 21, Claim 1, Line 32, after "represents" insert --a--.

Column 21, Claim 7, Line 67, "glycvrrhetinic" should read --glycyrrhetinic--.

Column 22, Claim 10, Line 52, after "A" insert --in--.

Column 22, Claim 11, Line 56, after "A" insert --in--.

Signed and Sealed this  
Twenty-sixth Day of December, 2017

Joseph Matal  
*Performing the Functions and Duties of the*  
*Under Secretary of Commerce for Intellectual Property and*  
*Director of the United States Patent and Trademark Office*